United States Patent [19]

Yoshida

[11] Patent Number: 4,617,465
[45] Date of Patent: Oct. 14, 1986

[54] RADIATION DETECTOR VESSEL

[75] Inventor: Yuzo Yoshida, Ootawara, Japan

[73] Assignee: Kabushiki Kaisha Toshiba, Japan

[21] Appl. No.: 610,695

[22] Filed: May 16, 1984

[30] Foreign Application Priority Data

May 23, 1983 [JP] Japan .................................. 58-89195

[51] Int. Cl.⁴ .............................................. G01T 1/185
[52] U.S. Cl. .................................... 250/385; 250/374
[58] Field of Search .................. 250/374, 385; 378/19, 378/161

[56] References Cited

U.S. PATENT DOCUMENTS

| 4,031,396 | 6/1977 | Whetten et al. | 250/385 |
| 4,073,400 | 2/1978 | Brook et al. | 220/453 |
| 4,260,891 | 4/1981 | Williams | 250/385 |
| 4,276,476 | 6/1981 | Cotic | 250/385 |
| 4,414,473 | 11/1983 | Hoffman et al. | 250/366 |

FOREIGN PATENT DOCUMENTS 57-49879 3/1982 Japan .
2027262 2/1980 United Kingdom .

OTHER PUBLICATIONS

Arfman & Gangulee, Preformed Beryllium Windows, 20 IBM Technical Disclosure Bulletin 5381-82 (May 1978).

Primary Examiner—Carolyn E. Fields
Attorney, Agent, or Firm—Finnegan, Henderson, Farabow, Garrett & Dunner

[57] ABSTRACT

A radiation detector has a housing in which is sealed a gas to be ionized when X-rays are projected therein. A plurality of electrodes for detecting the X-rays are arranged in the housing, and the housing is curved with a fixed curvature along the arranged direction of the electrodes. A vessel portion of the housing is closed by a cover portion. A cut extending in the longitudinal direction of the housing is formed in one side wall of the vessel portion. The cut is closed by an X-ray window. A window member of the X-ray window is made of carbon fiber reinforced plastics. The window member is bonded to the inside face of the side wall of the vessel portion, and is pressed against the inside face by the pressure of the gas sealed in the housing. Thus, the window member and the vessel portion are fully hermetically sealed. Since the X-ray transmission factor of the carbon fiber reinforced plastics is high, even low-energy X-rays can be projected with high intensity between the electrodes.

7 Claims, 8 Drawing Figures

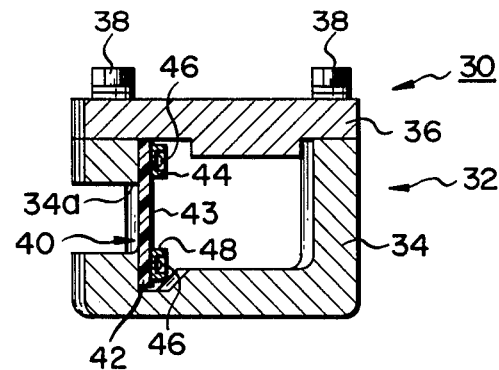
F I G. 4
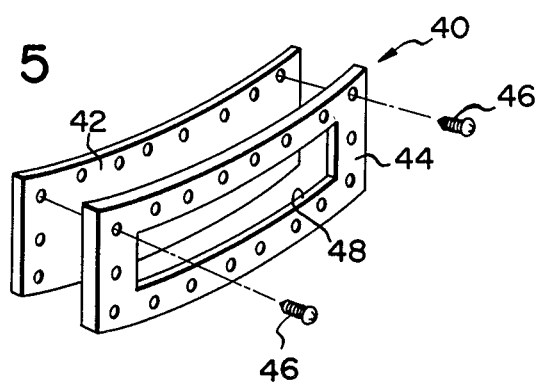
F I G. 5

RADIATION DETECTOR VESSEL

BACKGROUND OF THE INVENTION

The present invention relates to a radiation detector used in a sectional radiographic apparatus such as a computerized tomographic (hereafter abbreviated as CT) apparatus.

In a CT apparatus, as shown in FIG. 1, a fan-shaped distribution of X-ray beam 12 is provided by an X-ray source 10. A radiation detector 14, comprising a plurality of detecting elements 16 arranged for detecting the intensity of the X-ray beam 12, faces the X-ray source 10 with a subject body 18 between them. While maintaining this positional relation, the X-ray source 10 and the radiation detector 14 are rotated around the subject body 18. In this state, the intensity of the X-ray beam 12 transmitted through the subject body 18 in various directions is detected. Detection data obtained in this manner are analyzed by a computer, and X-ray absorption factors for plane sections of the subject body 18 taken along those different directions are calculated. The cross sections of the subject body 18 are given in gradations based on the X-ray absorption factors, thus forming a sectional image. In this CT apparatus, the plane sections of the subject body 18 can be analyzed in as many as 2,000 gradations, depending on the composition of the subject body 18. Thus, a clear sectional image can be obtained for any tissue ranging from soft to hard tissue.

In the radiation detector 14, as shown in FIGS. 1 to 3, electrodes, as the detecting elements 16, are spacially arranged from one another in a housing 20. High-pressure Xe gas is sealed in the housing 20. When the X-ray beam 12 is projected into the interelectrode space on the extension of the X-ray beam 12 through an X-ray window 22 of the housing 20, the Xe gas existing in the space is ionized to produce $Xe^+$ ions and electrons. The $Xe^+$ ions and electrons are detected as ionization currents by the electrodes, which are integrated for a predetermined time. The integrated currents are discharged by a discharge circuit having a predetermined time constant. The intensity of X-ray beam can be calculated from the value of the discharge time.

The performance of a radiation detector is judged by its sensitivity and resolution (space resolution and density resolution). The quality of an image reconstructed on a CT apparatus is influenced by the performance of the radiation detector. The sensitivity of the radiation detector is given as the product (atm.cm; hereafter referred to as PL value) of the pressure of gas sealed in the radiation detector and the depth of electrodes. Usually, the sensitivity is in the vicinity of 60 atm.cm. In this case, the coefficient of energy absorption ranges from 40 to 60%. The space resolution of the radiation detector, which depends on the arrangement pitch of the electrodes and focus spot size of X-ray tube, is such that the detector can normally discriminate a substance with a diameter of 0.5 to 0.6 mm. The density resolution is related to the capability of distinguishing substances with small differences in density in a subject body. If the radiation detector is higher in density resolution, then it can discriminate smaller differences in density in proportion. The density resolution depends on the amount of low-energy photons which are transmitted through the X-ray window of the radiation detector to reach the interelectrode space therein. This is so because definite discrimination of white and gray matter in the subject body requires detection of the low-energy photons, since the difference in the coefficient of X-ray absorption between the white and gray matter is increased in proportion if the energy of the photons is lower.

The housing 20 of the radiation detector 14 is provided with the X-ray window 22 for the incidence of X-ray beams, which is thinner than any other portion of the housing 20. Also, the housing 20, including the X-ray window 22, is made of aluminium. However, the X-ray window 22 cannot avoid absorption of low-energy photons, failing to provide satisfactory density resolution.

A radiation detector using a carbon-fibered structure as its X-ray window is disclosed in U.S. Pat. No. 4,260,891. In this radiation detector, a carbon-fibered plate is sandwiched between a pressure vessel and a clamping lid. Therefore, the carbon-fibered plate needs to serve both as the X-ray window and as a sealing gasket between the clamping lid and the pressure vessel. Thus, this X-ray window is flat in shape. In a radiation detector, the X-ray beam has, generally, fan-shaped distribution, so that the X-ray window is curved around the X-ray source 10 for improved detection accuracy. It is difficult, however, to seal gas at a high pressure of 10 to 30 atm in the housing while keeping the carbon-fibered X-ray window curved. Accordingly, any of prior art radiation detectors is low in practicality.

SUMMARY OF THE INVENTION

The object of the present invention is to provide a radiation detector capable of holding gas therein in a hermetically sealed state and of providing high density resolution.

According to the invention, there is provided a radiation detector which has a plurality of radiation detecting elements and converts the intensity of radiation into an electric signal. The radiation detector comprises an elongated housing, curved along the longitudinal direction thereof and having a gas sealed therein, and a plurality of radiation detecting elements arranged therein along the longitudinal direction thereof. The housing includes a vessel portion in which are arranged the radiation detecting elements; the vessel portion having an opening through which the radiation detecting elements are loaded into the housing; a side wall on the side of the center of curvature; a cut in the side wall extending along the longitudinal direction of the housing; and a cover portion covering the opening. A radiation window allows radiation to be led into the housing. The radiation window includes a window member, formed of carbon-fiber-reinforced-plastics, curved along and fixed to the inside face of the side wall so as to cover the cut. The window member is also pressed against the inside face of the side wall by the pressure of the gas sealed in the housing.

In this radiation detector, radiation such as an X-ray is transmitted through the window member to be detected by the radiation detecting elements in the housing. Since the X-ray transmission factor of the carbon-fiber-reinforced-plastics is higher than that of aluminium, even low-energy radiation can reach the radiation detecting elements with high intensity. Accordingly, the radiation detector of the invention is high in density resolution, and can provide high-quality sectional images when it is incorporated in a CT apparatus.

In this radiation detector, moreover, the opening through which the radiation detecting elements are loaded into the housing and the cut for the radiation window are provided separately. The junction between the cover portion covering the opening and the vessel portion is tightly sealed by the conventional sealing means to prevent leakage of the sealed gas. The gas will never leak through the junction between the window member and the vessel portion, since the window member is bonded to the side wall of the vessel portion and is also fixed by means of a reinforcing member as required. The window member is pressed against the side wall by the pressure of the sealed gas. Namely, the window member is attached to the housing in a self-sealing manner, so that the junction between the radiation window and the housing can be sealed with improved gastightness. Thus, the radiation detector according to this invention can hold the gas therein in a fully sealed manner.

BRIEF DESCRIPTION OF THE DRAWINGS

FIG. 4 is a sectional view of a radiation detector according to one embodiment of the present invention;

FIG. 5 is a disassembled perspective view of an X-ray window of the radiation detector of FIG. 4;

DETAILED DESCRIPTION OF THE PREFERRED EMBODIMENTS

Figure 1:
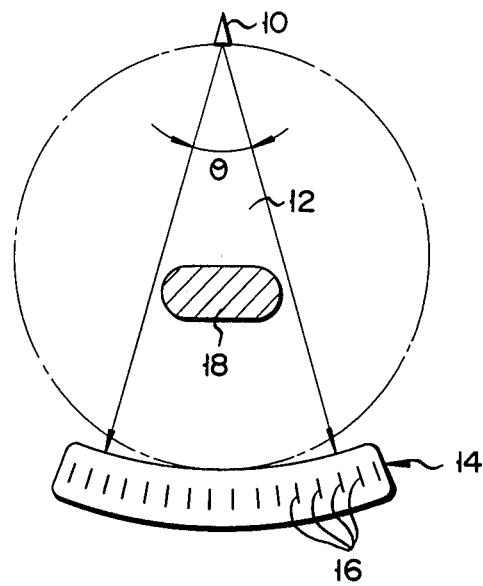
FIG. 1 is a schematic plan view of a CT apparatus.
Figure 2:
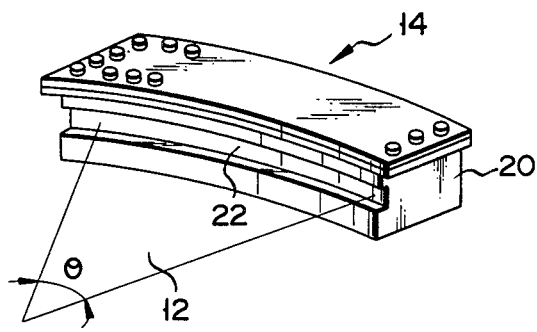
FIG. 2 is a perspective view of a conventional radiation detector.
Figure 3:
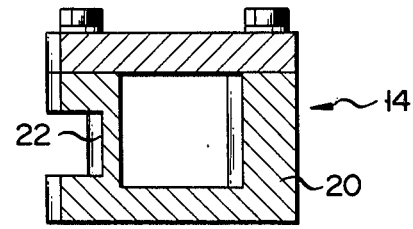
FIG. 3 is a sectional view of the radiation detector of FIG. 2.

Referring now to the drawings of FIGS. 4 and 5, there is shown a radiation detector 30 according to one embodiment of the present invention. The radiation detector 30 has a housing 32 and an X-ray window 40. The housing 32 includes a vessel portion 34 and a cover portion 36. As in the prior art radiation detector 14, the plane configuration of the housing 32 is curved around the X-ray source 10 for providing the fan-shaped distribution of X-ray beam 12 (see FIG. 1). Therefore, the side walls of the vessel portion 34 are curved along the longitudinal direction thereof. An elongated rectangular cut 34a, extending along the longitudinal direction of the vessel portion 34, is formed on the side wall of the vessel portion 34 toward the center of curvature. The cover portion 36 is placed on the top of the vessel portion 34. A suitable sealing gasket (not shown) is interposed between the cover portion 36 and the vessel portion 34, and these two portions 36 and 34 are fixed by means of bolts 38. The cover and vessel portions 36 and 34 are made of aluminium, which has a high X-ray transmission factor. A plurality of electrodes as X-ray detecting elements are specially arranged from one another along the longitudinal direction of the housing 32. These electrodes are set in the housing 32, which is fixed to the under surface of the cover portion 36.

An X-ray window 40 includes a window member 42 and a reinforcing member 44. The window member 42 is in the form of the curved plate, matched to the inside face of the side wall of the vessel portion 34 in which the cut 34a is formed. The reinforcing member 44 is a plate having substantially the same shape as the window member 42, except that the reinforcing member 44 has a cut 48 in the center which is a little larger than the cut 34a. The window member 42 is put on the inside face of its mating side wall of the vessel portion 34 so as to close the cut 34a therein. Further, the reinforcing member 44 is put on the window member 42. The reinforcing member 44 is fixed to the inside face of the side wall of the vessel portion 34 by means of bolts 46. Thus, the peripheral portion of the window member 42 is sandwiched between the side wall of the vessel portion 34 and the reinforcing member 44. In the example shown in FIGS. 4 and 5, the bolts 46 are screwed into the side wall of the vessel portion 34 through holes in the reinforcing member 44 and the window member 42. If the window member 42 is made smaller than the reinforcing member 44, however, it is unnecessary to provide the window member 42 with through holes.

The window member 42 is made of carbon fiber reinforced plastics (hereafter abbreviated CFRP). The CFRP is formed by heating acrylic fibers or rayon fibers to 200° to 300° C. to carbonize the same, then heating them to 700° to 1,800° C. for further carbonization, and finally impregnating resultant carbon fibers with resins (e.g., epoxy resins). The CFRP usually contains 60% fibers and 40% resins by volume, and has the following properties. The X-ray transmission factor of the CFRP is ten times (60 to 100 KV) that of aluminium of the same thickness (same transmission distance). The tensile strength of the CFRP in its fiber direction is about 120 kg/mm$^2$ Since the tensile strength of aluminium ranges from 50 to 60 kg/mm$^2$, the CFRP is approximately twice as strong as aluminium. The modulus of elasticity of the CFRP is about 12,000 kg/mm$^2$, which is a practical figure. Thus, the CFRP is much higher in X-ray transmission factor and strength than aluminium.

In this embodiment, a layer of aluminium foil 43 (bold line) of about 20-micron thickness is put on the convex surface of the curved CFRP plate by adhering aluminium film on the CFRP plate. Since the aluminium foil layer 43 is electrically conductive, the X-ray window 40 will not be charged even if Xe$^+$ ions and electrons produced by ionization of Xe gas in the vessel portion 34 are attached to the inner surface of the X-ray window 40. Impurity gases or outer gases are naturally generated from the CFRP. However, the aluminium foil layer 43 checks the generation of the outer gases, thereby preventing the outer gases from getting into the inside space of the housing 2.

The window member 42 is bonded, by means of an adhesive agent such as epoxy resins, to the inside face of the side wall of the vessel portion 34 in which the cut 34a is formed. In this case, the window member 42 and the side wall of the vessel portion 34 can be bonded together with increased strength by etching the inside face of the side wall to roughen the contact surface to 50 microns or thereabout. As described above, the window member 42 is pressed against the inside face of the side wall of the vessel portion 34 by the reinforcing member 44. Also, Xe gas at a pressure of 10 to 30 atm is sealed in the housing 32. The window member 42 is also pressed against the side wall of the vessel portion 34 by the pressure of the sealed gas. Thus, the window member 42 is sealed and fixed to the side wall by the adhesive agent and the reinforcing member 44, and is also pressed against the side wall by the sealed gas pressure, that is, is self-sealed, so that the gastightness of the housing 32 is very high.

In this radiation detector, an X-ray beam passes through the X-ray window 40 formed of CFRP to reach the electrodes (not shown) in the housing 32. Since the CFRP is twice as strong as aluminium, as mentioned before, the thickness of the X-ray window may be made half that of an aluminium X-ray window. Also, the X-ray transmission factor of the CFRP is ten times that of aluminium. Therefore, the amount of X-ray transmission, i.e., the amount of X-rays reaching the electrodes (detecting elements), can be increased, theoretically, about twenty times. Thus, the density resolution is increased. As a result, the signal-to-noise ratio is improved, and the X-ray window absorbs less low-energy X-rays. Accordingly, the radiation detector can positively distinguish white and gray matters which differ little in absorption coefficient.

Figure 8:
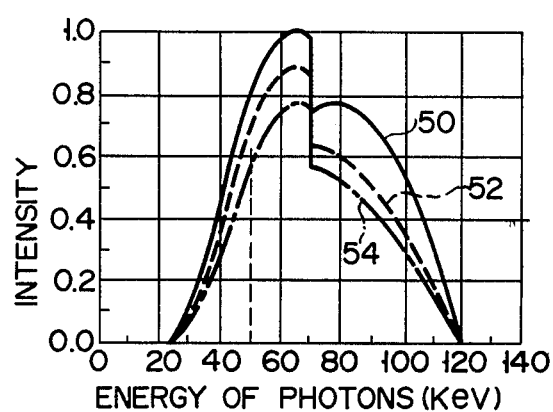
FIG. 8 is a graph showing effects of the invention.

FIG. 8 is a graph showing X-ray spectra obtained before and after transmission of X-rays through the X-ray window. The axis of abscissa of the graph represents the energy of photons, and the axis of ordinate represents the intensity of X-rays. In FIG. 8, line 50 (solid line) indicates an X-ray absorption spectrum obtained before the transmission through the X-ray window 40; line 52 (broken line) indicates an absorption spectrum of X-rays transmitted through the X-ray window made of CFRP, and line 54 (dashed line) indicates an absorption spectrum of X-rays transmitted through the X-ray window made of aluminium. The spectrum line K-X is not shown in FIG. 8. As seen from FIG. 8, the X-ray absorption of the detector on the lowenergy side obtained by using the CFRP is 15 to 20% larger than that obtained by using aluminium. The X-ray windows used for comparing the results represented by lines 52 and 54 have the same thickness. Since CFRP is higher in strength than aluminium, the X-ray window made of CFRP can be made relatively thin, and can therefore be lowered in X-ray absorption.

Figure 6:
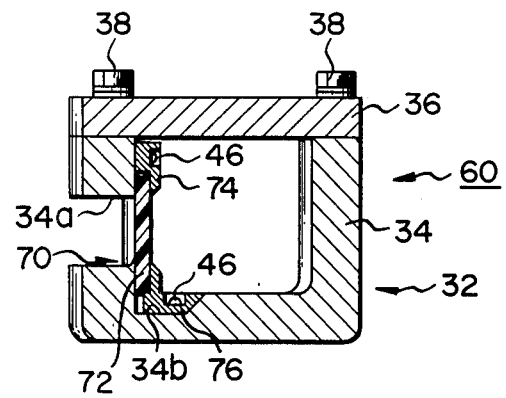
FIG. 6 is a sectional view of a radiation detector according to another embodiment of the invention.
Figure 7:
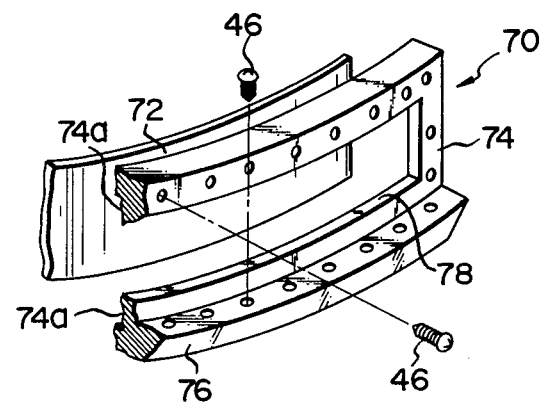
FIG. 7 is a partial disassembled perspective view of an X-ray window of the radiation detector of FIG. 6.

Referring now to FIGS. 6 and 7, another embodiment of the invention will be described. This embodiment differs from the first embodiment only in the construction of the X-ray window. In FIGS. 6 and 7, like reference numerals are used to designate like members included in the first embodiment, and description of those members is omitted. A radiation detector 60 according to this second embodiment has a housing 32 and an X-ray window 70. A curved groove 34b extending along the longitudinal direction of a vessel portion 34 of the housing 32 is formed in the vicinity of a cut 34a in the bottom wall of the vessel portion 34.

Like the window member 42 and the reinforcing member 44, a window member 72 and a reinforcing member 74 are curved around the X-ray source 10. The reinforcing member 74 has a cut 78 resembling the cut 48 of the reinforcing member 44. A recess 74a in which the window member 72 is fitted is formed in that surface of the reinforcing member 74 which is put on the window member 72, i.e., that surface on the side of the center of curvature. The depth of the recess 74a is less than the thickness of the window member 72. An engaging portion 76 extending along the longitudinal direction of the reinforcing member 74 is formed at the lower end portion thereof. That lateral face of the engaging portion 76 on the opposite side to the recess 74a is inclined relative to the bottom wall of the vessel portion 34. Thus, the cross section of the engaging portion 76 is in the form of a trapezoid with its shorter side downward. The engaging portion 76 is fitted in the groove 34b. The window member 72 is put on the inside face of that side wall of the vessel portion 34 in which the cut 34a is formed, and the reinforcing member 74 is put on the window member 72 in a manner such that the window member 72 is fitted in the recess 74a, and that the engaging portion 76 is fitted in the groove 34b. The frame portion and the engaging portion 76 of the reinforcing member 74 are fixed to the side wall and the bottom wall of the vessel portion 34, respectively, by means of bolts 46. In this embodiment, the window member 72 is not provided with any holes through which the bolts 46 are passed. Thus, the X-ray window 70 is free from concentrated stress on the peripheral regions of the holes, and is therefore higher in strength than the X-ray window 40.

Also in this embodiment, the window member 72 is bonded to the side wall of the vessel portion 34 by means of an adhesive agent. Moreover, the window member 72 is pressed against the side wall of the vessel portion 34 by the pressure of gas sealed in the housing 32, and the engaging portion 76 of the reinforcing member 74 is urged downward by the gas pressure. As a result, the whole structure of the reinforcing member 74 is urged toward the window member 72 by the interaction of the respective slanted surfaces of the engaging portion 76 and the groove 34b. Thus, the window member 72 is brought into closer contact with the side wall of the vessel portion 34 for satisfactory sealing.

What is claimed is:

1. A radiation detector vessel enclosing a plurality of radiation detecting elements that convert the intensity of radiation into an electric signal, comprising:

an elongated housing curved along the longitudinal direction thereof in which a gas is sealed, said housing including a vessel member having an opening of sufficient size to allow loading of the radiation detecting elements into said vessel member and a cover member covering said opening of said vessel member, said vessel member further including a bottom interior face, a side wall on the side of the center of curvature, a cut in said side wall extending along the longitudinal direction of said housing, and an egagement groove in said bottom face adjacent said side wall, said engagement groove extending in the longitudinal direction of said housing and having a bottom face, a first side face adjacent said side wall, and a second side face spaced from said side wall, wherein said second side face inclines away from said side wall;

a radiation window through which radiation is led into said housing, said radiation window including a window member formed of carbon fiber reinforced plastic and curved in conformity with an inside face of said side wall to cover said cut, said window member being pressed against said inside face of said side wall by the pressure of the gas sealed in said housing;

reinforcing means connected to said inside face of said side wall of said housing for holding said window member between said reinforcing means and said inside face of said side wall of said housing, said reinforcing means including a reinforcing member having an engagement portion extending in the longitudinal direction of said housing and fitting into said engagement groove, said engagement portion having an inclined face slidably contacting said second side face of said engagement groove; and means for urging said engagement portion of said reinforcing member toward said bottom face of said engagement groove to slide said engagement portion along said second side face of said engagement groove toward said side wall to press said window member against said inside face of said side wall of said housing.

2. The radiation detector vessel according to claim 1, wherein said radiation window has metal foil covering that surface of the window member located inside the housing.

3. The radiation detector vessel according to claim 2, wherein said metal foil is aluminium foil.

4. The radiation detector vessel according to claim 1, wherein peripheral portions of said reinforcing member are connected to the inside face of the side wall by bolts.

5. The radiation detector vessel according to claim 4, wherein said peripheral portions of said reinforcing member include through holes through which said bolts are screwed into said inside face of said wall.

6. The radiation detector vessel according to claim 1, wherein said gas sealed in the housing is xenon gas.

7. The radiation detector vessel according to claim 1, wherein said urging means includes bolts and said engagement portion of said reinforcing member includes through holes through which said bolts are screwed into said bottom face of said engagement groove.

* * * * *